United States Patent [19]

Louis et al.

[11] Patent Number: 4,970,238

[45] Date of Patent: Nov. 13, 1990

[54] 3-AMINOPROPOXYPHENYL DERIVATIVES, THEIR PREPARATION AND PHARMACEUTICAL COMPOSITIONS CONTAINING THEM

[75] Inventors: W. John Louis, 3, Balmoral Avenue, Kew, 3101 Victoria, Australia; Richard Berthold, Bottmingen, Switzerland; André Stoll, Birsfelden, Switzerland

[73] Assignee: John William Louis, Australia

[21] Appl. No.: 321,815

[22] Filed: Mar. 10, 1989

Related U.S. Application Data

[60] Division of Ser. No. 22,502, Mar. 9, 1987, Pat. No. 4,816,604, which is a continuation of Ser. No. 790,576, Oct. 23, 1985, abandoned, which is a continuation of Ser. No. 691,497, Jan. 14, 1985, abandoned, which is a continuation of Ser. No. 481,775, Apr. 4, 1983, abandoned, which is a continuation of Ser. No. 281,459, Jul. 8, 1981, abandoned.

[30] Foreign Application Priority Data

| Jul. 9, 1980 | [GB] | United Kingdom | 8022412 |
| Aug. 7, 1980 | [CH] | Switzerland | 5999/80 |
| Nov. 6, 1980 | [CH] | Switzerland | 8247/80 |
| Nov. 6, 1980 | [CH] | Switzerland | 8245/80 |
| Dec. 23, 1980 | [GB] | United Kingdom | 8041155 |
| Feb. 13, 1981 | [GB] | United Kingdom | 8104585 |

[51] Int. Cl.⁵ .......................................... A61K 31/135
[52] U.S. Cl. ................................... 514/652; 514/620; 514/618; 514/534; 514/531; 514/530; 514/529; 514/524; 514/427

[58] Field of Search ............... 560/1, 55, 65, 73, 106, 560/107, 122, 123, 124; 564/349, 165, 162; 548/563; 558/414, 416, 422; 514/427, 524, 529, 530, 531, 534, 618, 620, 652

[56] References Cited

U.S. PATENT DOCUMENTS

| 3,949,088 | 4/1976 | Samuelsson et al. | 424/324 |
| 4,171,370 | 10/1979 | Jonas et al. | 564/349 |
| 4,252,984 | 2/1981 | Manoury et al. | 260/465 |

FOREIGN PATENT DOCUMENTS 7605 7/1979 European Pat. Off. .

Primary Examiner—Nicky Chan
Attorney, Agent, or Firm—Sughrue, Mion, Zinn, Macpeak & Seas

[57] ABSTRACT

The compounds of formula I,

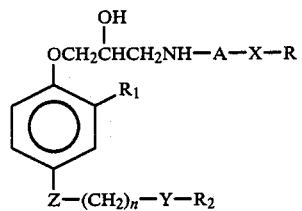

where the substituents have various significances, and physiologically acceptable hydrolyzable derivatives thereof having the hydroxy group in the 2 position of the 3-aminopropoxy side chain in esterified form, are useful as cardioselective β-adrenoceptor blocking agents.

21 Claims, No Drawings

3-AMINOPROPOXYPHENYL DERIVATIVES, THEIR PREPARATION AND PHARMACEUTICAL COMPOSITIONS CONTAINING THEM

This is a division of application Ser. No. 07/022,502 filed Mar. 9, 1987, now U.S. Pat. No. 4,816,604 which is a continuation of application Ser. No. 06/790,576 filed Oct. 23, 1985, abandoned, which is a continuation of Ser. No. 06/691,497 filed Jan. 14, 1985, abandoned, which is a continuation of Ser. No. 06/481,775 filed Apr. 4, 1983, abandoned, which is a continuation of Ser. No. 06/281,459 filed on July 8, 1981 abandoned.

The present invention relates to 3-aminopropoxyphenyl derivatives, their preparation and pharmaceutical compositions containing them.

In accordance with the invention there are provided compounds of formula I,

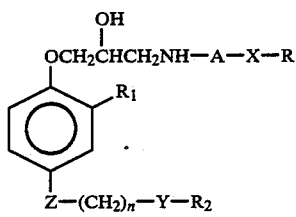

wherein
R is phenyl or phenyl monosubstituted or independently disubstituted or independently trisubstituted by alkyl of 1 to 4 carbon atoms, alkoxy of 1 to 4 carbon atoms or halogen of atomic number of from 9 to 35, $R_1$ is hydrogen, alkyl of 1 to 4 carbon atoms, alkoxy of 1 to 4 carbon atoms, alkylthio of 1 to 4 carbon atoms, cycloalkyl of 3 to 7 carbon atoms, halogen of atomic number of from 9 to 53, trifluoromethyl, 1-pyrrolyl, cyano, carbamoyl, alkenyl of 2 to 5 carbon atoms; alkenyloxy of 3 to 5 carbon atoms wherein the double bond is not attached to the carbon atom adjacent to the oxygen atom, or alkanoyl of 1 to 5 carbon atoms, $R_2$ is alkyl of 1 to 4 carbon atoms, cycloalkyl of 5 to 7 carbon atoms, cycloalkylalkyl of 3 to 7 carbon atoms in the cycloalkyl moiety and of 1 to 4 carbon atoms in the alkyl moiety, phenyl, phenylalkyl of 7 to 10 carbon atoms, or phenyl or phenylalkyl of 7 to 10 carbon atoms monosubstituted or independently disubstituted or independently trisubstituted in the phenyl ring by alkyl of 1 to 4 carbon atoms, alkoxy of 1 to 4 carbon atoms or halogen of atomic number of from 9 to 35, A is alkylene of 2 to 5 carbon atoms,
X is a bond, an oxygen or a sulfur atom,
Y is an oxygen or a sulfur atom, and either Z is an oxygen atom and n is 2 or 3 or Z is a bond and n is 1, 2 or 3, with the provisos that (a) when $R_2$ is alkyl, then Z is an oxygen atom and the group —NH—A—X—R is other than the moiety of formula

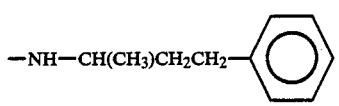

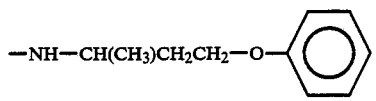

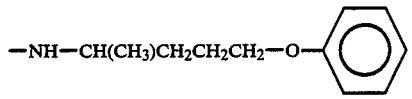

or

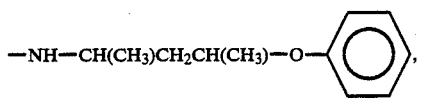

(b) when $R_2$ is alkyl and X is a bond or an oxygen atom, then Y is an oxygen atom, and (c) when $R_2$ is unsubstituted or monosubstituted phenyl, X is a bond and Z is an oxygen atom, or when $R_2$ is cycloalkyl or cycloalkylalkyl and X is a bond, then $R_1$ is other than hydrogen, and physiologically acceptable hydrolyzable derivatives thereof having the hydroxy group in the 2 position of the 3-aminopropoxy side chain in esterified form.

Physiologically hydrolyzable derivatives are those derivatives which under physiological conditions are split to the corresponding compounds having a hydroxy group in the 2 position of the 3-aminopropoxy side chain.

A group of derivatives in esterified form of the compounds of formula I is e.g. the compounds of formula E,

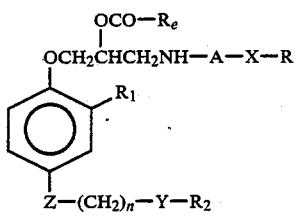

wherein
R, $R_1$, $R_2$, A, X, Y, Z and n are as defined above and $R_e$ is alkyl of 1 to 12 carbon atoms, cycloalkyl of 3 to 7 carbon atoms, phenyl, phenylalkyl of 7 to 12 carbon atoms, or phenyl or phenylalkyl of 7 to 12 carbon atoms monosubstituted in the phenyl ring by alkyl of 1 to 4 carbon atoms, or mono- or independently disubstituted in the phenyl ring by halogen of atomic number of from 9 to 35, or mono- or independently di- or independently trisubstituted in the phenyl ring by alkoxy of 1 to 4 carbon atoms.

Any trisubstituted phenyl ring preferably is substituted by alkoxy; preferably the substituents are identical.

Preferred are the compounds wherein the hydroxy group in the 2 position of the 3-aminopropoxy side chain is in unesterified form.

"Alkylene" only comprises radicals having a carbon chain of at least 2 carbon atoms separating X from the nitrogen atom of the 3-aminopropoxy side chain.

Alkyl and/or alkoxy and/or alkylthio preferably are of 1 or 2 carbon atoms, especially of 1 carbon atom. Halogen preferably is chlorine or bromine, especially bromine Cycloalkyl preferably is of 3, 5 or 6 carbon atoms, especially 5 or 6 carbon atoms, when it is $R_1$, and preferably of 5 or 6 carbon atoms, when it is $R_2$. Alkenyl preferably is of 2 or 3 carbon atoms, it especially is allyl. Alkenyloxy preferably is of 3 or 4 carbon atoms, it especially is allyloxy. Cycloalkylalkyl is especially of 3, 5 or 6 carbon atoms in the cycloalkyl moiety and especially of 1 or 2 carbon atoms in the alkyl moiety, it preferably is cyclopropylmethyl. Phenylalkyl preferably is of 7 or 8 carbon atoms, it especially is benzyl.

A preferably is ethylene When A is of more than 2 carbon atoms, then it preferably is trimethylene or a moiety branched in the a position, such as —CH(CH$_3$)CH$_2$—, —C(CH$_3$)$_2$CH$_2$— or —C(CH$_3$)$_2$(CH$_2$)$_2$—. Conveniently, when $R_2$ is alkyl, A preferably is unbranched X preferably is a bond or an oxygen atom, especially an oxygen atom. R preferably is substituted phenyl, preferably mono- or disubstituted, especially monosubstituted. It preferably is substituted by alkoxy. When it is monosubstituted, it preferably is substituted in the para position. When it is disubstituted, it preferably is substituted in the meta and para positions. When it is trisubstituted, it preferably is substituted in the meta, meta and para positions. When $R_1$ is alkanoyl it is preferably acetyl. $R_1$ preferably is hydrogen, cycloalkyl, alkenyl, halogen or cyano, especially hydrogen or cyano. $R_2$ preferably is alkyl, cycloalkylalkyl or phenylalkyl, especially cycloalkylalkyl or phenylalkyl. When $R_2$ is phenyl or phenylalkyl, it preferably is substituted, preferably mono- or disubstituted, especially monosubstituted. It preferably is substituted by alkoxy. When it is monosubstituted phenyl or phenylalkyl, it preferably is substituted in the para position. When it is disubstituted phenyl or phenylalkyl, it preferably is substituted in the meta and para positions. When it is trisubstituted phenyl or phenylalkyl, it preferably is substituted in the meta, meta and para positions. Y preferably is an oxygen atom. n preferably is 2. Z preferably is an oxygen atom.

When a phenyl ring is polysubstituted, the substituents preferably are identical.

A group of compounds of the invention is the compounds of formula Ia,

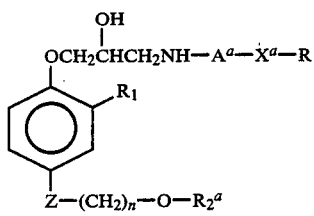

wherein

R, $R_1$, n and Z are as defined above, $R_2^a$ with the exception of alkyl of 1 to 4 carbon atoms has the significance indicated above for $R_2$, $A^a$ is alkylene of 2 to 5 carbon atoms and $X^a$ is an oxygen or a sulfur atom, and physiologically acceptable hydrolyzable derivatives thereof having the hydroxy group in the 2 position of the 3-aminopropoxy side chain in esterified form.

In a sub-group $R_1$ in formula Ia is other than hydrogen.

Another group of compounds of the invention is the compounds of formula Ib,

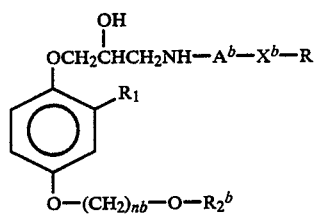

wherein

R and $R_1$ are as defined above, $R_2^b$ is alkyl of 1 to 4 carbon atoms, $A^b$ is ethylene or trimethylene, $X^b$ is a bond or an oxygen atom and nb is 2 or 3 and physiologically acceptable hydrolyzable derivatives thereof having the hydroxy group in the 2 position of the 3-aminopropoxy side chain in esterified form.

In a subgroup $R_1$ in formula Ib is other than hydrogen. In another subgroup $X^b$ is an oxygen atom.

Another group of compounds of the invention is the compounds of formula Ipa,

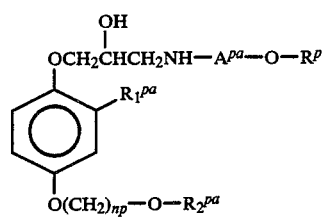

wherein $R^p$ is phenyl or phenyl monosubstituted or independently disubstituted or independently trisubstituted by alkoxy of 1 to 4 carbon atoms, $R_1^{pa}$ is hydrogen or halogen of atomic number of from 9 to 35, $R_2^{pa}$ is alkyl of 1 to 4 carbon atoms, $A^{pa}$ is alkylene of 2 to 5 carbon atoms and np is 2 or 3, with the proviso that —NH—$A^{pa}$—O—$R^p$ is other than the moiety of formula

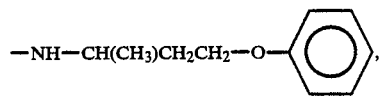

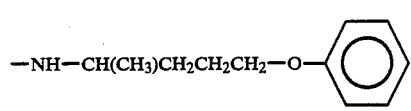

or

Another group of compounds of the invention is the compounds of formula Ipb,

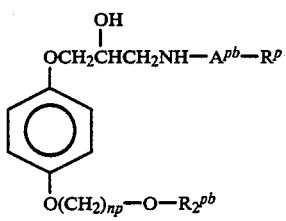   Ipb wherein

R$^p$ and np are as defined above,

R$_2^{pb}$ is alkyl of 1 to 4 carbon atoms and

A$^{pb}$ is alkylene of 2 to 5 carbon atoms, with the proviso that —NH—A$^{pb}$—R$^p$ is other than the moiety of formula

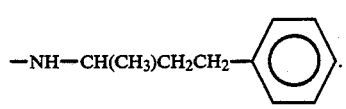

Another group of compounds of the invention is the compounds of formula Ipc,

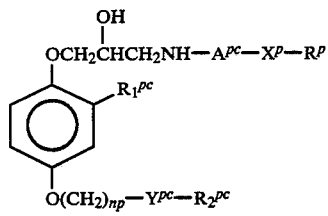   Ipc wherein

R$^p$ and np are as defined above,

Y$^{pc}$ is an oxygen or a sulfur atom,

R$_1^{pc}$ is 1-pyrrolyl, cyano or carbamoyl,

R$_2^{pc}$ is alkyl of 1 to 4 carbon atoms or cycloalkylalkyl of 3 to 7 carbon atoms in the cycloalkyl moiety and of 1 to 4 carbon atoms in the alkyl moiety, A$^{pc}$ is alkylene of 2 to 5 carbon atoms and X$^p$ is an oxygen or sulfur atom, with the provisos that, (a) when R$_2^{pc}$ is alkyl, then —NH—A$^{pc}$—X$^p$—R$^p$ is other than the moiety of formula

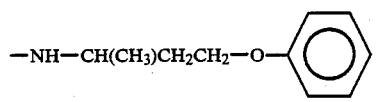

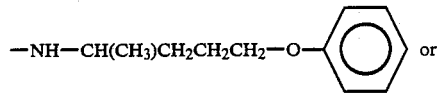 or

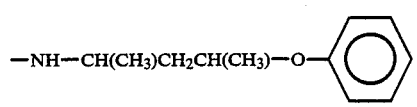

and (b) when R$_2^{pc}$ is alkyl and X$^p$ is an oxygen atom, then Y$^{pc}$ is an oxygen atom.

Another group of compounds of the invention is the compounds of formula Ipd,

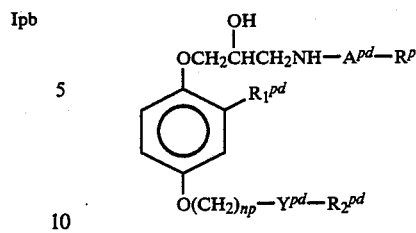   Ipd wherein

R$^p$ and np are as defined above,

Y$^{pd}$ is an oxygen or a sulfur atom,

R$_1^{pd}$ and R$_2^{pd}$ have the significance indicated above for R$_1^{pc}$ and R$_2^{pc}$, respectively, and A$^{pd}$ is alkylene of 2 to 5 carbon atoms, with the provisos that, (a) when R$_2^{pd}$ is alkyl, then —NH—A$^{pd}$—R$^p$ is other than the moiety of formula

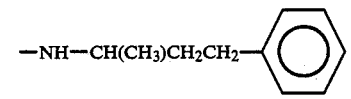

and (b) when R$_2^{pd}$ is alkyl, then Y$^{pd}$ is an oxygen atom.

Another group of compounds of the invention is the compounds of formula Ipe,

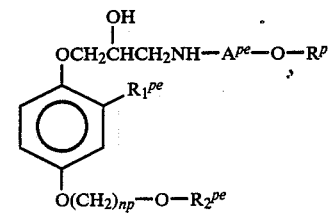   Ipe wherein

R$^p$ and np are as defined above,

R$_1^{pe}$ is hydrogen, halogen of atomic number of from 9 to 35 or cyano;

R$_2^{pe}$ is phenyl or phenyl monosubstituted or independently disubstituted or independently trisubstituted by alkoxy of 1 to 4 carbon atoms and A$^{pe}$ is alkylene of 2 to 5 carbon atoms.

Conveniently R$^p$ in formulae Ipa to Ipe is substituted phenyl.

Another group of compounds of the invention is the compounds of formula Is,

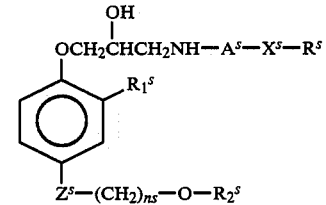   Is wherein

R$^s$ is phenyl or phenyl monosubstituted or independently disubstituted by alkoxy of 1 to 4 carbon atoms, $R_1{}^s$ is hydrogen, halogen of atomic number of from 9 to 35, cyano, carbamoyl, alkenyl of 2 to 5 carbon atoms or cycloalkyl of 5 or 6 carbon atoms $R_2{}^s$ is alkyl of 1 to 4 carbon atoms, cyclopropylmethyl, phenylalkyl of 7 or 8 carbon atoms or phenylalkyl of 7 or 8 carbon atoms monosubstituted or independently disubstituted in the phenyl ring by alkoxy of 1 to 4 carbon atoms, $A^s$ is ethylene or trimethylene, $X^s$ and $Z^s$ independently are a bond or an oxygen atom and $n^s$ is 2 or 3, with the provisos that, (a) when $R_2{}^s$ is alkyl, then $Z^s$ is an oxygen atom and (b) when $R_2{}^s$ is cyclopropylmethyl and $X^s$ is a bond, then $R_1{}^s$ is other than hydrogen, and physiologically acceptable hydrolyzable derivatives thereof having the hydroxy group in the 2 position of the 3-aminopropoxy side chain in esterified form.

In a subgroup $R_1{}^s$ in formula Is is other than hydrogen. In another subgroup $R_2{}^s$ is other than alkyl.

In accordance with the invention, a compound of the invention may be obtained by a process comprising reacting a corresponding compound of formula II,

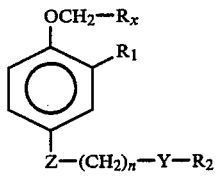

wherein $R_1$, $R_2$, Y, Z and n are as defined above and $R_x$ is a group capable of reacting with a primary amine to give a 2-amino-1-hydroxyethyl group, with an appropriate compound of formula III,

H₂N—A—X—R    III wherein A, X and R are as defined above, and, where required, appropriately esterifying the 2 position of the 3-aminopropoxy side chain in the resulting compound of formula I.

The amination process may be effected in conventional manner for the production of analogous 3-amino-2-hydroxypropoxyaryl compounds. For example, $R_x$ may be a group of formula

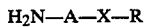

or a derivative of this group, e.g. a group of formula —CH(OH)—CH₂L, wherein L is chlorine, bromine or a group $R_y$—SO₂—O—, wherein $R_y$ is phenyl, tolyl or lower alkyl. L is especially chlorine. The reaction is preferably effected in ethanol or in an appropriate ether such as dioxane. Optionally an excess of the amine may be used as solvent. Alternatively, the reaction may be effected in a fusion melt. Suitable reaction temperatures may be from about 20° to about 200° C., conveniently the reflux temperature of the reaction mixture when a solvent is present.

The optional esterification of the 2 hydroxy group in the side chain may be effected in manner known for the production of analogous esters of 3-amino-2-hydroxypropoxyaryl compounds, if necessary using selective reactions when other reactive groups are present.

Free base forms of the compounds of the invention may be converted into acid addition salt forms in conventional manner and vice versa. Suitable acids for acid addition salt formation include hydrochloric, malonic and fumaric acids.

In the compounds of the invention, the carbon atom in e.g. the 2 position of the 3-aminopropoxy side chain is asymmetrically substituted. The compounds may thus exist in the racemic form or in individual optical isomer form. The preferred optical isomer has the S configuration at this asymmetrically substituted carbon atom of the 3-aminopropoxy side chain. Individual optical isomer forms may be obtained in conventional manner, for example by using optically active starting materials or by fractional crystallisation of racemate salts using optically active acids.

A compound used as a starting material may be obtained in conventional manner.

In particular, a compound of formula II may be obtained by introducing by b 0-alkylation a group —OCH₂—$R_x$ into a compound of formula IV,

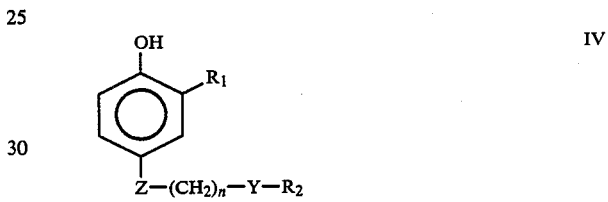

wherein $R_1$, $R_2$, Y, Z and n are as defined above. A compound of formula IV preferably is reacted in anionic form.

A compound of formula IVa

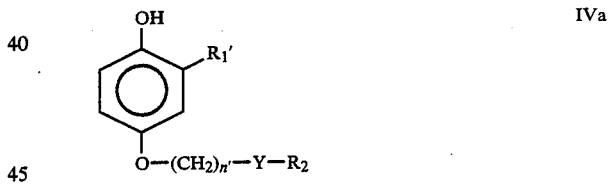

wherein $R_1'$ is hydrogen, alkyl of 1 to 4 carbon atoms, alkoxy of 1 to 4 carbon atoms, alkylthio of 1 to 4 carbon atoms, cycloalkyl of 3 to 7 carbon atoms, halogen of atomic number of from 9 to 53, 1-pyrrolyl, cyano, carbamoyl, alkenyl of 2 to 5 carbon atoms, alkenyloxy of 3 to 5 carbon atoms wherein the double bond is not attached to the carbon atom adjacent to the oxygen atom, or alkanoyl of 1 to 5 carbon atoms, $n'$ is 2 or 3 and Y and $R_2$ are as defined above, may e.g. be obtained by deprotecting a corresponding compound of formula V,

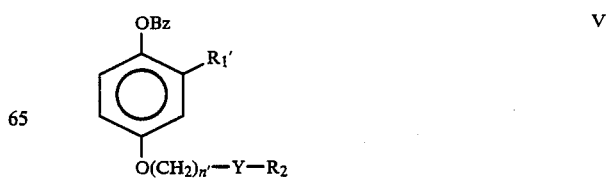

wherein $R_1'$, $R_2'$, and Y are as defined above and Bz is a protecting group, e.g. benzyl or tetrahydropyranyl, under appropriate conditions, e.g. with palladium on charcoal or by acidic hydrolysis.

A compound of formula IVb,

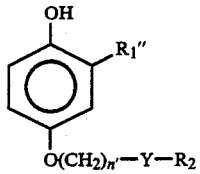

IVb wherein
$R_2$, Y and n' are as defined above and
$R_1''$ is alkylthio of 1 to 4 carbon atoms or trifluoromethyl,
may e.g. be obtained by selectively etherifying a corresponding 1,4-dihydroxy derivative at the hydroxy group in the meta position with respect to $R_1''$, e.g. by reaction with a molar equivalent of a compound of formula Hal —$(CH_2)_{n'}$—Y—R , wherein $R_2$,Y and n' are as defined above and Hal is halogen, preferably in an inert solvent such as acetone and in the presence of a base such as potassium carbonate.

A compound of formula Va,

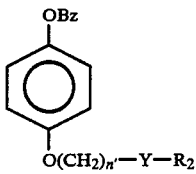

Va wherein Bz, Y, $R_2$ and n' are as defined above, may e.g. be obtained by appropriately etherifying 4-benzyloxyphenol, e.g. with an appropriate bromine derivative, conveniently in more than 1 step, e.g. by first forming the moiety —$O(CH_2)_{n'}$—Y—H and then alkylating to introduce the moiety $R_2$.

The compounds of formula Vb,

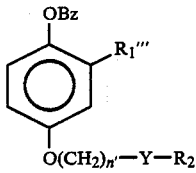

Vb wherein $R_2$, Y, n' and Bz are as defined above, and $R_1'''$ with the exception of hydrogen has the significance indicated above for $R_1'$, may e.g. be obtained by monochlorinating, -brominating or -iodinating a compound of formula IVa, wherein $R_1$ is hydrogen, in the position ortho to the hydroxy moiety, subsequently, if desired, appropriately protecting the hydroxy group in a resultant compound of formula IVa, wherein $P_1'$ is bromine, to obtain a compound of formula Vc,

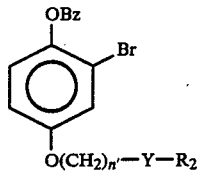

Vc wherein $R_2$, Y, n' and Bz are as defined above and subsequently, if desired, converting a compound of formula Vc, in a Grignard-type reaction, e.g. with lithium, to a corresponding compound of formula Vb, wherein $R_1'''$ is alkyl of 1 to 4 carbon atoms, cycloalkyl of 3 to 7 carbon atoms or alkenyl of 2 to 5 carbon atoms. Alternatively, a compound of formula Vc may be converted to a corresponding cyano compound, e.g. with cuprous cyanide in dimethyl formamide and subsequently, if desired, the cyano group hydrolyzed to a corresponding compound of formula Vb, wherein $R_1'''$ is carbamoyl. Subsequently, if desired, this carbamoyl compound may be converted in a Hofman type degradation into a corresponding amino derivative and this amino derivative converted e.g. with 2,5-dimethoxyfurane to a corresponding compound of formula Vb, wherein $R_1'''$ is 1-pyrrolyl. Alternatively, if desired, the amino derivative may be converted into a corresponding diazonium salt, e.g with nitrous acid, and this diazonium salt further reacted with e.g. potassium fluoride in water to a corresponding compound of formula Vb, wherein $R_1'''$ is fluorine. Alternatively, the diazonium salt may be converted by reaction with aqueous acid to a corresponding hydroxy compound and this hydroxy compound converted by etherification into a corresponding compound of formula Vb, wherein $R_1'''$ is alkoxy of 1 to 4 carbon atoms or alkenyloxy of 3 to 5 carbon atoms wherein the double bond is not attached to the carbon atom adjacent to the oxygen atom.

The $R_1'''$=alkanoyl derivative may be made by Friedel-Crafts acylation. If desired, the diazonium group may be converted into many other moieties, e.g. alkylthio by reaction with an alkali metal mercaptide. If required, the trifluoromethyl group may be obtained by fluorinating a corresponding carboxylic group which is in turn obtained from hydrolysing a cyano group.

Instead of Protected compounds of formula Vb it may be alternatively possible to use directly the corresponding unprotected compounds. For example, the group $R_1=\beta\gamma$-alkenyl may be introduced into the ortho position by subjecting the corresponding $\beta\gamma$-alkenyl ether to a Claisen rearrangement. If desired, the cyclopentyl group may be introduced by subjecting the corresponding cyclopent-2-enyl ether to a Claisen rearrangement to form the ortho cyclopent-2-enyl phenol which is then hydrogenated.

A compound of formula IVc,

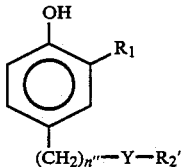

IVc wherein
$R_1$ and Y are as defined above,
$R_2'$ has the significance indicated above for $R_2$ and $n''$ is 1, 2 or 3, may e.g. be obtained essentially in analogous manner to that described above for the production of compounds of formula IVa from the corresponding protected compounds. If desired the protecting group may be methyl instead of benzyl or tetrahydropyranyl. The deprotecting reaction may be carried out in the presence of an alkali metal alkyl mercaptide.

The protected compounds wherein $R_1$ is other than hydrogen, alkylthio or trifluoromethyl may be produced in analogous manner to that described above for the production of compounds of formula Vb.

It may alternatively be possible to convert one substituent $R_1$ into another substituent when the compound is in unprotected form, e.g. orthobromo derivatives may be formed simply from the corresponding phenol.

The protected compounds wherein $R_1$ is hydrogen may be produced by building up the ether moiety —$(CH_2)n''$—Y—$R_2'$ in conventional manner, e.g. by a Williamson synthesis.

Insofar as the preparation of any particular starting material is not particularly described, this may be effected in conventional manner.

In the following Examples all temperatures are in degrees Centigrade and are uncorrected.

EXAMPLE 1:

2-{2-hydroxy-3-[2-(4-methoxyphenoxy)ethylamino]-propoxy}-5-(2-methoxyethoxy)benzonitrile 2.4 g of 2-(2,3-epoxypropoxy)-5-(2-methoxyethoxy)-benzonitrile and 8.35 g of 2-(4-methoxyphenoxy) ethylamine are dissolved in 30 ml of ethanol, the solvent is then evaporated and the resulting mixture stirred for 1 hour at 70°. The reaction melt is then dissolved in ether and allowed to crystallize under cooling. Purification is effected by recrystallization in benzene. The title compound is obtained (M.P. 95°-97°).

The starting material is obtained as follows:

Bromine dissolved in chloroform is added at 0° to a solution of 4-(2-methoxyethoxy)phenol (M.P. 98°-99°) [prepared by reacting 4-benzyloxyphenol with 2-chloroethyl methyl ether and debenzylating the resultant 1-benzyloxy-4-(2-methoxyethoxy) benzene (M.P. 41°-43°) by hydrogenation with palladium on charcoal] in methanol and the mixture stirred for 2 hours. After chromatography over silicagel, the resultant 2-bromo-4-(2-methoxyethoxy)phenol (oil) is reacted for 60 hours with a mixture of potassium carbonate, acetone and benzyl bromide. After chromatography over silicagel, the resultant 1-benzyloxy-2-bromo-4-(2-methoxyethoxy)benzene (oil) is reacted in dimethylformamide for 5 hours with cuprous cyanide. After purification by partition between aqueous hydrochloric acid solution and ethyl acetate, the resultant 2-benzyloxy-5-(2-methoxyethoxy)benzonitrile (M.P. 50°-51°) is debenzylated over 10% palladium on charcoal in methanol. The resultant 2-hydroxy-5-(2-methoxyethoxy)benzonitrile (oil) is reacted at 100° with epichlorhydrin and a catalytic amount of piperidine, and 2-(2,3-epoxypropoxy)-5-(2-methoxyethoxy)benzonitrile (oil) is obtained.

From the appropriate compounds of formula II, wherein $R_x$ is

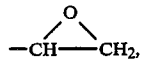

and the appropriate compounds of formula III the following compounds of formula I may be obtained in analogous manner to Example 1:

| Example No. | A | X | R | $R_1$ | $R_2$ | Y | Z | n | M.P. |
|---|---|---|---|---|---|---|---|---|---|
| 2(1) | ethylene | O | p-MeO-phenyl | H | cyclopropyl-methyl | 0 | 0 | 2 | b 99–101° |
| 3(2) | ethylene | O | p-MeO-phenyl | H | p-MeO-benzyl | 0 | 0 | 2 | b 97–98° |
| 4(3) | ethylene | O | p-MeO-phenyl | H | p-MeO-benzyl | 0 | bond | 2 | b 108–109.5° |
| 5 | ethylene | bond | m,p-di-MeO-phenyl | H | methyl | 0 | 0 | 2 | ch 143–144° |
| 6 | trimethylene | bond | phenyl | H | methyl | 0 | 0 | 2 | ch 175°(dec.) |
| 7 | ethylene | O | p-MeO-phenyl | H | methyl | 0 | 0 | 2 | b 113–115° |
| 8 | ethylene | O | m,p-di-MeO-phenyl | H | methyl | 0 | 0 | 2 | b 80–82° |
| 9 | ethylene | O | p-MeO-phenyl | Br | methyl | 0 | 0 | 2 | ch 133–135°(dec.) |
| 10 | ethylene | bond | m,p-di-MeO-phenyl | CN | methyl | 0 | 0 | 2 | b 93–95° |
| 11(4) | ethylene | O | p-MeO-phenyl | H | cyclopropyl-methyl | 0 | bond | 2 | b 90–91° |
| 12 | ethylene | O | phenyl | H | methyl | 0 | 0 | 2 | b 91–92° |
| 13(5) | ethylene | O | p-MeO-phenyl | $CONH_2$ | methyl | 0 | 0 | 2 | b 83–85° |
| 14 | ethylene | O | phenyl | Br | methyl | 0 | 0 | 2 | b 70–71° |
| 15 | ethylene | O | phenyl | CN | methyl | 0 | 0 | 2 | b 89–90° |
| 16 | trimethylene | bond | phenyl | CN | methyl | 0 | 0 | 2 | b 84–85° |
| 17 | trimethylene | bond | phenyl | Br | methyl | 0 | 0 | 2 | b 66–68° |
| 18 | ethylene | O | p-MeO-phenyl | CN | cyclopro- | 0 | 0 | 2 | b 64.5–65.5° |

-continued

| Example No. | A | X | R | R$_1$ | R$_2$ | Y | Z | n | M.P. |
|---|---|---|---|---|---|---|---|---|---|
| | | | | | pylmethyl | | | | | b = in free base form
dec. = decomposition
ch = in hydrochloride salt form
M.P. = melting point
MeO = methoxy

[1] 4-(2-Cyclopropylmethoxyethoxy)phenol(oil) — used as a starting material is obtained by reacting 4-benzyloxyphenol with 2-bromoethanol, reacting the resultant 4-(2-hydroxyethoxy)-1-benzyloxybenzene (M.P. 100–101°) with cyclopropyl-methylchloride, and debenzylating the resultant product (oil) by hydrogenation with palladium on charcoal.

[2] 4-[2-(4-Methoxybenzyloxy)ethoxy]phenol (oil) used as a starting material is obtained by reacting a mixture of hydroquinone, 2-(4-methoxybenzyloxy)ethyl chloride and potassium carbonate in dimethylformamide at 100° in an inert atmosphere and purifying the product by silicagel chromatography using toluene/ethyl acetate 19:1 as an eluent.

[3] 4-[2-(4-Methoxybenzyloxy)ethyl]phenol (oil) — used as a starting material is obtained by reacting 4-(2-bromoethyl)phenol with sodium 4-methoxybenzylalcoholate in tetrahydrofuran.

[4] As under[3], using sodium cyclopropylmethylate in lieu of 4-methoxybenzylalcoholate.

[5] 2-Hydroxy-5-(2-methoxyethoxy)benzamide used as starting material is obtained hydrolyzing 2-benzyloxy-5-(2-methoxyethoxy)benzonitrile with KOH in tert-butanol and debenzylating the resultant 2-benzyloxy-5-(2-methoxyethoxy)benzamide (M.P. 113–115°) by hydrogenation with palladium on charcoal.

The following compounds of formula I may also be obtained in a manner analogous to Example 1.

| Example No. | A | X | R 4-tolyl | R$_1$ | R$_2$ | Y | Z | n |
|---|---|---|---|---|---|---|---|---|
| A | —CH(CH$_3$)CH$_2$CH(CH$_3$)— | S | 4-tolyl | iPr | tBu | S | O | 3 |
| B | —CH$_2$C(CH$_3$)$_2$— | bond | 3,4,5-tri-MeO-phenyl | EtO | —CH$_2$CH(CH$_3$)—(cycloheptyl) | O | bond | 3 |
| C | —(CH$_2$)$_3$— | S | 2-Br,5-Me-phenyl | EtCO | cyclopentyl | O | bond | 3 |
| D | —(CH$_2$)$_3$— | S | 3-Br-phenyl | I | 4-iPr-phenyl | O | bond | 1 |
| E | —CH$_2$CH$_2$CH(CH$_3$)— | O | 3-Et,4-Cl-phenyl | tBuS | 2-(4-tolyl)ethyl | S | O | 3 |
| F | —(CH$_2$)$_3$— | bond | phenyl | CF$_3$ | —CH$_2$C(CH$_3$)$_2$—(2-OMe-phenyl) | O | O | 3 |
| G | —CH$_2$CH$_2$— | S | 4-tolyl | pyrrol-1-yl | —CH$_2$—(4-Br,...-Me-phenyl) | S | O | 2 |
| H | —(CH$_2$)$_3$— | bond | 2-Cl,6-iPrO-phenyl | vinyl | phenyl | O | O | 2 |
| I | —(CH$_2$)$_5$— | bond | 3,4,5-triMe-phenyl | OCH$_2$C=CCH$_3$ \| CH$_3$ or cyclobutyl | 4-(3,4,5-triMe-phenyl)butyl | O | bond | 3 |

Bu = n.butyl
EtO = ethoxy
iPr = isopropyl
iPrO = isopropoxy
Me = methyl
tBu = tert-butyl
tBuS = tert-butylthio The following derivatives, esters of the compounds of formula I (which are compounds of formula E) may be obtained by appropriately esterifying the 2 position of the 3-aminopropoxy side chain in the corresponding compounds of formula I (the other substituents are as for the corresponding compound of formula I):

| Ex. No. | Corresp. compound for formula I (Example No.) | R$_e$ (Formula E) |
|---|---|---|
| 1-E | 5 | n-nonyl |
| 2-E | 5 | 3-ethylbenzyl |

In a first group of compounds X is a bond.
In a 2nd group of compounds X is an oxygen atom.
In a 3rd group of compounds X is a sulfur atom.

In a 4th group of compounds R is mono- or disubstituted phenyl.

In a 5th group of compounds A is alkylene.

In a 6th group of compounds A is straight-chain alkylene.

In a 7th group of compounds $R_1$ is hydrogen.

In a 8th group of compounds $R_1$ is other than hydrogen.

In a 9th group of compounds $R_1$ is 1-pyrrolyl.

In a 10th group of compounds $R_1$ is cyano.

In a 11th group of compounds Z is an oxygen atom.

In a 12th group of compounds Z is a bond.

In a 13th group of compounds Y is an oxygen atom

In a 14th group of compounds Y is a sulfur atom.

In a 15th group of compounds $R_2$ is alkyl.

In a 16th group of compounds $R_2$ is cycloalkyl or cycloalkylalkyl.

In a 17th group of compounds $R_2$ is cycloalkylalkyl.

In a 18th group of compounds $R_2$ is unsubstituted or substituted phenyl or phenylalkyl.

In a 19th group of compounds $R_2$ is unsubstituted or substituted phenylalkyl.

In a 20th group of compounds $R_1$ is alkanoyl.

The compounds of the invention exhibit interesting pharmacological activity.

In particular, the compounds possess β-adrenoceptor blocking activity, as indicated by standard tests. For example, in the spontaneously beating guinea pig atrium (A. Bertholet et al, *Postgrad. Med.* 57, Suppl.1 [1981]9–18) they inhibit the positive chonotropic isoprenaline effect at bath concentrations of from about $10^{-8}$ M to about $10^{-6}$ M.

Some of the compounds, e.g. the compounds of Examples 12, 14 and 15 also exhibit α-blocking activity as indiqated in standard tests. For example the activity is observed in the everted rat aorta (according to the principles of K.K.F.Ng, S. Duffy, W.J. Louis and A.E. Doyle (1975); *Proceedings of the Australian Physiological and Pharmacological Society*, 6, 158P). The activity is also confirmed in binding studies, e.g. basically as described by R.J. Summers, B. Jarrott and W.J. Louis *Neuroscience letters* 20(1980) 347–350.

The compounds are therefore useful as β- and also α-adrenoceptor blocking agents, e.g. for the prophylaxis and therapy of coronary diseases, such as angina pectoris, conditions which are associated with sympathetic over-stimulation, e.g. nervous heart complaints, myocardial infarction, hypertension, for the intermediate treatment of migraine and for the treatment of glaucoma and thyrotoxicosis. In view of their antiarrhythmic effect, they are useful as antiarrhythmics for the treatment of disturbances in the heart rhythm, such as supraventricular tachycardia.

For these uses, the dosage to be used varies of course according to the substance used, the mode of administration and the desired treatment. In general, however, satisfactory results are obtained with a daily dosage of approximately 0.1 to 10 mg per kg body weight; administration may be effected in 2 to 4 divided doses, or in sustained release form. For the larger mammal, the daily dosage is from about 10 to about 500 mg; suitable forms for oral administration generally contain from about 2.5 to about 250 mg of the compounds together with solid or liquid carriers and/or diluents.

The compounds have more marked and wider spread beneficial pharmacological properties than could be expected for compounds having this type of structure. In particular their activity is more cardioselective than could be expected from similar known compounds. This cardioselectivity can be demonstrated in vitro by the use of isolated tissues of the guinea-pig, in accordance with standard procedures. Thus, left ventricular and lung membranes of a guinea-pig can be prepared according to standard pharmacological procedures (G. Engel et al., *Triangle* 19 [1980]69–76) and made to react with an exogenously added radioactive β-ligand such as I125 2-cyano-pindolol (I-CYP) to determine affinity of the test compound to $\beta_1$ and $\beta_2$ adrenoceptors.

For the compound of Example 1, the cardioselectivity amounts to about 80 times, for the compound of Example 2, to about 410 times, for the compound of Example 3, to about 170 times and for the compound of Example 7, to about 640 times.

Guinea pig lung and left ventricular membranes may e.g. be prepared as follows:

Adult guinea pigs (350–500g) are killed by decapitation. The heart and lung are perfused with Tris saline buffer (Tris-HCl 10 mM, pH=7.5, NaCl 0.154 M, 37° C.), removed and freed from connective tissues and trachea. The lung membranes are prepared as described by Kleinstein, J. and Glossmann H., *Naunyn-Schmiedeberg's Arch. Pharmacol.* 305, [1978], 191–200 with the modification that medium A contains only 20 mM $NaHCO_3$. The final pellet is suspended in 10 ml 20 mM $NaHCO_3$ and stored in liquid nitrogen. The preparation of the left ventricle membranes follows the procedure published by McNamara, D.B. et al., *J. Biochem.* 75, [1974], 795–803 until the step where the 'membrane fraction' is received. These membranes are stored in liquid nitrogen and immediately before use further diluted to the appropriate concentrations as indicated in the text.

The compounds of Examples 1 to 18 exhibit effective β-adrenoceptor blocking activity in the above in vitro tests at concentrations of $10^{-9}$ M to $10^{-5}$ M.

The high selectivity of blockade for these compounds is of major importance in the treatment of hypertension where exacerbation of an existing asthmatic condition may be precipitated by currently commercially available compounds.

The compounds also possess a degree of intrinsic sympathomimetic activity, a property which is useful in preventing undue bradycardia and helps reduce the incidence of heart failure in subjects with heart muscle disease.

Of the compounds in optically active form, those in which the carbon atom in the 2-position of the 3-aminopropoxy side chain has the (S)-configuration are pharmacologically more active than the corresponding (R)-enantiomers.

The preferred uses of the compounds are the use against coronary diseases and hypertension.

Preferred are the compounds of Examples 1,2, 3 and 11, especially of Examples 1 and 3.

The compounds in free form or in the form of their pharmaceutically acceptable acid addition salts may be administered alone or in suitable dosage forms. The present invention also provides a pharmaceutical composition comprising a compound of the invention in free base form or in acid addition salt form in association with a pharmaceutical carrier or diluent. Such forms, e.g. a solution or a tablet, may be produced according to known methods.

We claim:

1. A method of treating coronary diseases, conditions resulting from sympathetic overstimulation, myocardial infarction, hypertension, migraine, glaucoma, thyrotoxicosis or heart rhythm disorders, which comprises administering to an animal in need of such treatment a therapeutically effective amount of a compound of formula I,

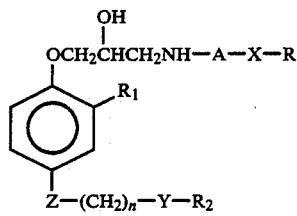

wherein
R is phenyl or phenyl monosubstituted or independently disubstituted or independent trisubstituted by alkyl of 1 to 4 carbon atoms, alkoxy of 1 to 4 carbon atoms or halogen of atomic number of from 9 to 35,
$R_1$ is hydrogen, alkyl of 1 to 4 carbon atoms, alkoxy of 1 to 4 carbon atoms, alkylthio of 1 to 4 carbon atoms, cycloalkyl of 3 to 7 carbon atoms, halogen of atomic number of from 9 to 53, trifluoromethyl, 1-pyrrolyl, cyano, carbamoyl, alkenyl of 2 to 5 carbon atoms, alkenyloxy of 3 to 5 carbon atoms wherein the double bond is not attached to the carbon atom adjacent to the oxygen atom, or alkanoyl of 1 to 5 carbon atoms,
$R_2$ is alkyl of 1 to 4 carbon atoms, cycloalkyl of 3 to 7 carbon atoms, cycloalkylalkyl of 3 to 7 carbon atoms in the cycloalkyl moiety and of 1 to 4 carbon atoms in the alkyl moiety, phenyl, phenylalkyl of 7 to 10 carbon atoms, or phenyl or phenylalkyl of 7 to 10 carbon atoms monosubstituted or independently disubstituted or independently trisubstituted in the phenyl ring by alkyl of 1 to 4 carbon atoms, alkoxy of 1 to 4 carbon atoms or halogen of atomic number of from 9 to 35,
A is alkylene of 2 to 5 carbon atoms,
X is a bond, an oxygen or a sulfur atom,
Y is an oxygen or a sulfur atom, and either
Z is an oxygen atom and
n is 2 or 3 or
Z is a bond and
n is 1, 2 or 3, with the provisos, that
(a) when $R_2$ is alkyl, then Z is an oxygen atom and the group —NH—A—X—R is other than a moiety of the formula

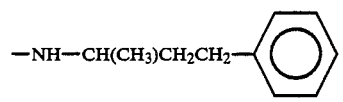

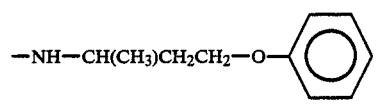

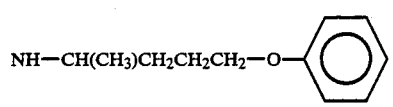

or

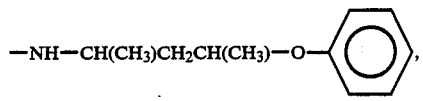

(b) when $R_2$ is alkyl and X is a bond or an oxygen atom, then Y is an oxygen atom, and
(c) when $R_2$ is cycloalkyl or cycloalkylalkyl and X is a bond, or
when $R_2$ is unsubstituted or monosubstituted phenyl,
X is a bond and
Z is an oxygen atom,
then $R_1$ is other than hydrogen, or a physiologically acceptable hydrolyzable derivative thereof having the hydroxy group in the 2 position of the 3-aminopropoxy side chain in esterified form, or a pharmaceutically acceptable acid addition salt form thereof.

2. A method of effecting β-adrenoceptor blockade, which comprises administering to an animal in need of such treatment a therapeutically effective amount of a compound of formula I,

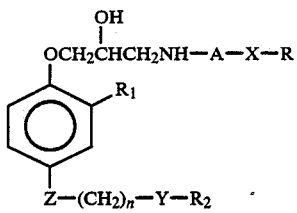

wherein
R is phenyl or phenyl monosubstituted or independently disubstituted or independent trisubstituted by alkyl of 1 to 4 carbon atoms, alkoxy of 1 to 4 carbon atoms or halogen of atomic number of from 9 to 35,
$R_1$ is hydrogen, alkyl of 1 to 4 carbon atoms, alkoxy of 1 to 4 carbon atoms, alkylthio of 1 to 4 carbon atoms, cycloalkyl of 3 to 7 carbon atoms, halogen of atomic number of from 9 to 53, trifluoromethyl, 1-pyrrolyl, cyano, carbamoyl, alkenyl of 2 to 5 carbon atoms, alkenyloxy of 3 to 5 carbon atoms wherein the double bond is not attached to the carbon atom adjacent to the oxygen atom, or alkanoyl of 1 to 5 carbon atoms,
$R_2$ is alkyl of 1 to 4 carbon atoms, cycloalkyl of 3 to 7 carbon atoms, cycloalkylalkyl of 3 to 7 carbon atoms in the cycloalkyl moiety and of 1 to 4 carbon atoms in the alkyl moiety, phenyl, phenylalkyl of 7 to 10 carbon atoms, or phenyl or phenylalkyl of 7 to 10 carbon atoms monosubstituted or independently disubstituted or independently trisubstituted in the phenyl ring by alkyl of 1 to 4 carbon atoms, alkoxy of 1 to 4 carbon atoms or halogen of atomic number of from 9 to 35,
A is alkylene of 2 to 5 carbon atoms,
X is a bond, an oxygen or a sulfur atom,
Y is an oxygen or a sulfur atom, and either
Z is an oxygen atom and
is 2 or 3 or
Z is a bond and
is 1, 2 or 3, with the provisos, that (a) when R₂ is alkyl, then Z is an oxygen atom and th group —NH—A—X—R is other than a moiety of the formula

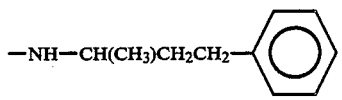

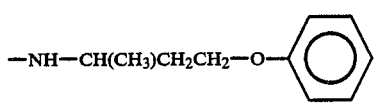

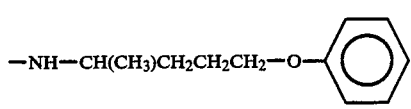

or

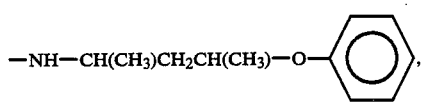

(b) when R₂ is alkyl and X is a bond or an oxygen atom, they Y is an oxygen atom, and
(c) when R₂ is cycloalkyl or cycloalkylalkyl and X is a bond, or
when R₂ is unsubstituted or monosubstituted phenyl,
X is a bond and
Z is an oxygen atom,
then R₁ is other than hydrogen, or a physiologically acceptable hydrolyzable derivative thereof having the hydroxy group in the 2 position of the 3-aminopropoxy side chain in esterified form, or a pharmaceutically acceptable acid addition salt form thereof.

3. A method of claim 1 or 2, wherein said compound of the formula I has the formula E,

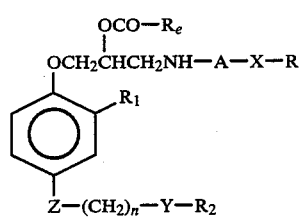

wherein
R, R₁, R₂, A, X, Y, Z and n are as defined in claim 4 and
$R_e$ is alkyl of 1 to 12 carbon atoms, cycloalkyl of 3 to 7 carbon atoms, phenyl, phenylalkyl of 7 to 12 carbon atoms, or phenyl or phenylalkyl of 7 to 12 carbon atoms monosubstituted in the phenyl ring by alkyl of 1 to 4 carbon atoms, or mono- or independently disubstituted in the phenyl ring by halogen of atomic number of from 9 to 35, or mono- independently di- or independently trisubstituted in the phenyl ring by alkoxy of 1 to 4 carbon atoms.

4. A method of claim 1 or 2, wherein said compound of formula I has formula Ia,

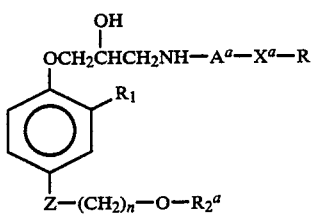

wherein
R, R₁, n and Z are as defined in claim 4 or 5,
$R_2^a$ has the significance indicated in claim 4 or 5 for R₂ with the exception that $R_2^a$ is not alkyl of 1 to 4 carbon atoms,
$A^a$ is alkylene of 2 to 5 carbon atoms and
$X^a$ is an oxygen or a sulfur atom, or a physiologically acceptable hydrolyzable derivative thereof having the hydroxy group in the 2 position of the 3-aminopropoxy side chain in esterified form.

5. A method of claim 4, wherein R₁ in formula Ia is other than hydrogen.

6. A method of claim 1 or 2 wherein said compound of formula I has formula Ib,

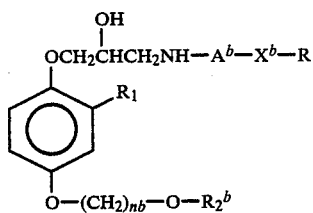

wherein
R and R₁ are as defined in claim 4 or 5,
$R_2^b$ is alkyl of 1 to 4 carbon atoms,
$A^b$ is ethylene or trimethylene,
$X^b$ is a bond or an oxygen atom and
nb is 2 or 3, or a physiologically acceptable hydrolyzable derivative thereof having the hydroxy group in the 2 position of the 3-aminopropoxy side chain in esterified form.

7. A method of claim 6, wherein R₁ is other than hydrogen.

8. A method of claim 6, wherein $X^b$ is an oxygen atom.

9. A method of claim 1 or 2, wherein said compound of formula I has formula Ipa,

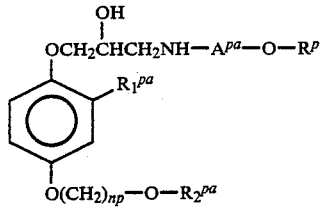

wherein
$R^p$ is phenyl or phenyl monosubstituted or independently disubstituted or independently trisubstituted by alkoxy of 1 to 4 carbon atoms,
$R_1^{pa}$ is hydrogen or halogen of atomic number of from 9 to 35,
$R_2^{pa}$ is alkyl of 1 to 4 carbon atoms,
$A^{pa}$ is alkylene of 2 to 5 carbon atoms, and np is 2 or 3, with the proviso that —N-
H—$A^{pa}$—O—$R^p$ is other than the moiety of the
formula

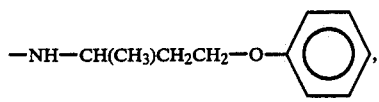

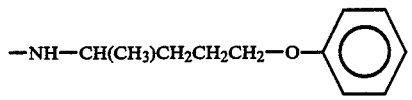

or

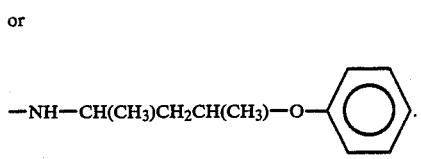

10. A method of claim 1 or 2, wherein said compound of formula I has formula Ipb,

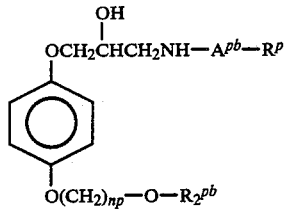 Ipb wherein
$R^p$ is phenyl or phenyl monosubstituted or independently disubstituted or independently trisubstituted by alkoxy of 1 to 4 carbon atoms,
$R_2^{pb}$ is alkyl of 1 to 4 carbon atoms,
$A^{pb}$ is alkylene of 2 to 5 carbon atoms, and
nb is 2 or 3 with the proviso that —NH—$A^{pb}$—$R^p$ is other than the moiety of the formula

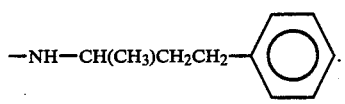

11. A method of claim 1 or 2, wherein said compound of formula I has formula Ipc,

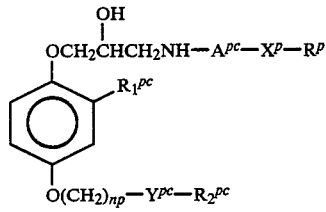 Ipc wherein
$R^p$ is phenyl or phenyl monosubstituted or independently disubstituted or independently trisubstituted by alkoxy of 1 to 4 carbon atoms,
$Y^{pc}$ is an oxygen or a sulfur atom,
$R_1^{pc}$ is 1-pyrrolyl, cyano or carbamoyl, $R_2^{pc}$ is alkyl of 1 to 4 carbon atoms or cycloalkylalkyl of 3 to 7 carbon atoms in the cycloalkyl moiety and of 1 to 4 carbon atoms in the alkyl moiety,
$A^{pc}$ is alkylene of 2 to 5 carbon atoms,
$X^p$ is an oxygen or sulfur atom, and
np is 2 to 3 with the proviso that,
(a) when $R_2^{pc}$ is alkyl, then —NH—$A^{pc}$—$X^p$—$R^p$ is other than the moiety of the formula

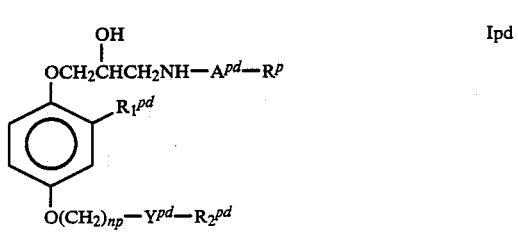

or

—NH—CH(CH₃)CH₂CH(CH₃)—O—⟨phenyl⟩, (b) when $R_2^{pc}$ is alkyl and $X^p$ is an oxygen atom, then $Y^{pc}$ is an oxygen atom.

12. A method of claim 1 or 2, wherein said compound of formula I has formula Ipd, OH    Ipd
|
OCH₂CHCH₂NH—$A^{pd}$—$R^p$
$R_1^{pd}$ O(CH₂)ₙₚ—$Y^{pd}$—$R_2^{pd}$ wherein
$R^p$ is phenyl or phenyl monosubstituted or independently disubstituted or independently trisubstituted by alkoxy of 1 to 4 carbon atoms,
$Y^{pd}$ is an oxygen or a sulfur atom,
$R_1^{pd}$ is 1-pyrrolyl, cyano or carbamoyl,
$R_2^{pd}$ is alkyl of 1 to 4 carbon atoms or cycloalkyl of 3 to 7 carbon atoms in the cycloalkyl moiety and of 1 to 4 carbon atoms in the alkyl moiety,
$A^{pd}$ is alkylene of 2 to 5 carbon atoms, and
np is 2 or 3 with the proviso that,
(a) when $R_2^{pd}$ is alkyl, then —NH—$A^{pd}$—$R^p$ is other than the moiety of the formula

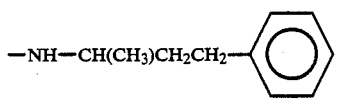

and
(b) when $R_2^{pd}$ is alkyl, then $Y^{pd}$ is an oxygen atom.

13. A method of claim 1 or 2, wherein said compound of formula I has formula Ipe,

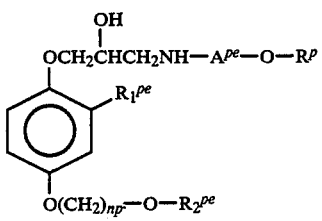

Ipe

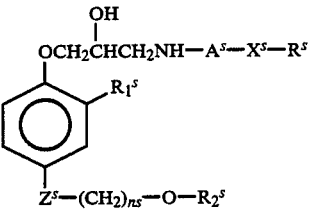

Is wherein
- $R^p$ is phenyl or phenyl monosubstituted or independently disubstituted or independently trisubstituted by alkoxy of 1 to 4 carbon atoms,
- $R_1^{pe}$ is hydrogen, halogen or atomic number of from 9 to 35 or cyano,
- $R_2^{pe}$ is phenyl or phenyl monosubstituted or independently disubstituted or independently trisubstituted by alkoxy of 1 to 4 carbon atoms,
- $A^{pe}$ is alkylene of 2 to 5 carbon atoms, and
- np is 2 or 3.

14. A method of claim 9, wherein $R^p$ is substituted phenyl.

15. A method of claim 10, wherein $R^p$ is substituted phenyl.

16. A method of claim 11, wherein $R^p$ is substituted phenyl.

17. A method of claim 12, wherein $R^p$ is substituted phenyl.

18. A method of claim 13, wherein $R^p$ is substituted phenyl.

19. A method of claim 1 or 2, wherein said compound of formula I has formula Is,

- $R^s$ is phenyl or phenyl monosubstituted or independently disubstituted by alkoxy of 1 to 4 carbon atoms,
- $R_1^s$ is hydrogen, halogen of atomic number of from 9 to 35, cyano, carbamoyl, alkenyl of 2 to 5 carbon atoms or cycloalkyl of 5 or 6 carbon atoms,
- $R_2^s$ is alkyl of 1 to 4 carbon atoms, cyclopropylmethyl, phenylalkyl of 7 or 8 carbon atoms or phenylalkyl of 7 or 8 carbon atoms monosubstituted or independently disubstituted in the phenyl ring by alkoxy of 1 to 4 carbon atoms,
- $A^s$ is ethylene or trimethylene,
- $X^s$ and $Z^s$ independently are a bond or an oxygen atom and
- ns is 2 or 3, with the proviso that,
  (a) when $R_2^s$ is alkyl, then $Z^s$ is an oxygen atom and
  (b) when $R_2^s$ is cyclopropylmethyl and $X^s$ is a bond, then $R_1^s$ is other than hydrogen, or a physiologically acceptable hydrolyzable derivative thereof having the hydroxy group in the 2 position of the 3-aminopropoxy side chain in esterified form.

20. A method of claim 19, wherein $R_1^s$ is other than hydrogen.

21. A method of claim 19, wherein $R_2^s$ is other than alkyl.

* * * * *

UNITED STATES PATENT AND TRADEMARK OFFICE
CERTIFICATE OF CORRECTION

PATENT NO.  : 4,970,238
DATED       : November 13, 1990
INVENTOR(S) : William J. Louis, et. al.

It is certified that error appears in the above-identified patent and that said Letters Patent is hereby corrected as shown below:

On the cover page of Patent, please correct Inventor and Assignee information to read as follows:

[75] Inventors:  William J. Louis, 3, Balmoral Avenue, Kew, 3101 Victoria, Australia; Richard Berthold, Bottmingen, Switzerland; Andre Stoll, Birsfelden, Switzerland

[73] Assignee:   William John Louis, Australia

Signed and Sealed this

Fifteenth Day of December, 1992

Attest:

DOUGLAS B. COMER

*Attesting Officer*    *Acting Commissioner of Patents and Trademarks*